(12) United States Patent
Soito et al.

(10) Patent No.: US 7,794,413 B2
(45) Date of Patent: Sep. 14, 2010

(54) LIBRARIES AND DATA STRUCTURES OF MATERIALS REMOVED BY DEBULKING CATHETERS

(75) Inventors: Angela Soito, Oakland, CA (US); John B. Simpson, Woodside, CA (US)

(73) Assignee: EV3, Inc., Plymouth, MN (US)

( * ) Notice: Subject to any disclaimer, the term of this patent is extended or adjusted under 35 U.S.C. 154(b) by 713 days.

(21) Appl. No.: 11/230,924

(22) Filed: Sep. 21, 2005

(65) Prior Publication Data

US 2006/0236019 A1 Oct. 19, 2006

Related U.S. Application Data

(63) Continuation-in-part of application No. 11/108,887, filed on Apr. 19, 2005.

(51) Int. Cl.
- *A61B 5/103* (2006.01)
- *A61B 5/117* (2006.01)
- *A61B 10/00* (2006.01)
- *G06F 7/00* (2006.01)
- *G06F 17/30* (2006.01)

(52) U.S. Cl. .................. 600/587; 600/562; 707/802

(58) Field of Classification Search ................. 600/300, 600/301, 308, 562, 587; 128/920, 923, 925; 707/100, 104.1; 703/11
See application file for complete search history.

(56) References Cited

U.S. PATENT DOCUMENTS

| | | | |
|---|---|---|---|
| 2,178,790 A | 11/1939 | Henry | |
| 3,705,577 A | 12/1972 | Sierra | |
| 3,815,604 A | 6/1974 | O'Malley et al. | |
| 3,837,345 A | 9/1974 | Matar | |
| 3,995,619 A | 12/1976 | Glatzer | |
| 4,210,146 A | 7/1980 | Banko | |
| 4,669,469 A | 6/1987 | Gifford et al. | |
| 4,696,298 A | 9/1987 | Higgins et al. | |
| 4,771,774 A | 9/1988 | Simpson et al. | |
| 4,781,186 A | 11/1988 | Simpson et al. | |
| 4,817,613 A | 4/1989 | Jaraczewski et al. | |
| 4,819,635 A | 4/1989 | Shapiro | |
| 4,850,957 A | 7/1989 | Summers | |
| 4,926,858 A | 5/1990 | Gifford, III et al. | |
| RE33,258 E | 7/1990 | Onik et al. | |
| 4,966,604 A | 10/1990 | Reiss | |
| 4,979,951 A | 12/1990 | Simpson | |
| 4,986,807 A | 1/1991 | Farr | |
| 4,994,067 A | 2/1991 | Summers | |
| 5,024,651 A | 6/1991 | Shiber | |
| 5,047,040 A | 9/1991 | Simpson et al. | |
| 5,053,044 A | 10/1991 | Mueller et al. | |
| 5,071,425 A | 12/1991 | Gifford et al. | |
| 5,084,010 A | 1/1992 | Plaia et al. | |
| 5,087,265 A | 2/1992 | Summers | |
| 5,092,873 A | 3/1992 | Simpson et al. | |
| 5,154,724 A | 10/1992 | Andrews | |
| 5,181,920 A | 1/1993 | Mueller et al. | |
| 5,217,474 A | 6/1993 | Zacca et al. | |
| 5,222,966 A | 6/1993 | Perkins et al. | |
| 5,224,488 A | 7/1993 | Neuffer | |
| 5,224,949 A | 7/1993 | Gomringer et al. | |
| 5,226,909 A | 7/1993 | Evans et al. | |
| 5,226,910 A | 7/1993 | Kajiyama et al. | |
| 5,242,460 A | 9/1993 | Klein et al. | |
| 5,250,059 A | 10/1993 | Andreas et al. | |
| 5,250,065 A | 10/1993 | Clement et al. | |
| 5,269,793 A | 12/1993 | Simpson et al. | |
| 5,282,484 A | 2/1994 | Reger | |
| 5,285,795 A | 2/1994 | Ryan et al. | |
| 5,312,425 A | 5/1994 | Evans et al. | |
| 5,318,032 A | 6/1994 | Lonsbury et al. | |
| 5,318,528 A | 6/1994 | Heaven et al. | |
| 5,321,501 A | 6/1994 | Swanson et al. | |
| 5,372,602 A | 12/1994 | Burke | |
| 5,395,313 A | 3/1995 | Naves et al. | |

(Continued)

FOREIGN PATENT DOCUMENTS

| | | |
|---|---|---|
| CA | 1002205 | 12/1976 |
| EP | 0 999 447 A1 | 5/2000 |
| WO | WO 03/016910 A1 | 2/2003 |
| WO | WO 2004/089184 A2 | 10/2004 |

OTHER PUBLICATIONS

Yoffe et al., "Preliminary Experience with the Xtrak Debulking Device in the Treatment of Peripheral Occulasions", Journal of Endovascular Therapy, vol. 9, No. 2, pp. 234-240.

"MollRing Cutter", Vascular Architects, www.vasculararchitects.com/pages/products_MollRing_Intl.html, Sep. 28, 2004.

Takagi et al., "Effective Plaque Removal With a New 8 French-Compatible Atherectomy Catheter", Catheter Cardiovasc Interv., Aug. 2002, vol. 56, No. 5, pp. 452-459.

"Flexi-Cut® Directional Debulking System: Indications, Contraindications, Warnings, Precautions, Adverse Effects", www.guidant.com/products/ProductTemplates/VI/dca_ifu.shtml, Sep. 29, 2004.

Rosenthal et al., "Remote Superficial Femoral Artery Endarterectomy and Distal aSpite Stenting: Multicenter Medium-Term Results", Journal of Vascular Surgery, Jul. 2004, vol. 40, No. 1, pp. 67-72.

(Continued)

*Primary Examiner*—Max Hindenburg
*Assistant Examiner*—Jeffrey G Hoekstra
(74) *Attorney, Agent, or Firm*—Mintz, Levin, Cohn, Ferris, Glovsky and Popeo P.C.

(57) ABSTRACT

Material removed by a debulking catheter from a body lumen can be preserved. Materials can be collected from many different patients and/or from multiple procedures on individual patients. Data which describe the properties or qualities of the removed material and/or the patient and/or the patient's family or environment can be stored on computer readable media. The stored data can be used to draw correlations, to stratify groups of patients, to provide risk assessments, to provide diagnoses and/or prognoses. Further tests can be done on the stored materials at later times after the procedures have been completed.

19 Claims, No Drawings

U.S. PATENT DOCUMENTS

| | | |
|---|---|---|
| 5,403,334 A | 4/1995 | Evans et al. |
| 5,419,774 A | 5/1995 | Willard et al. |
| 5,429,136 A | 7/1995 | Milo et al. |
| 5,431,673 A | 7/1995 | Summers et al. |
| 5,441,510 A | 8/1995 | Simpson et al. |
| 5,459,570 A | 10/1995 | Swanson et al. |
| 5,470,415 A | 11/1995 | Perkins et al. |
| 5,485,042 A | 1/1996 | Burke et al. |
| 5,491,524 A | 2/1996 | Hellmuth et al. |
| 5,505,210 A | 4/1996 | Clement |
| 5,507,292 A | 4/1996 | Jang et al. |
| 5,507,760 A | 4/1996 | Wynne et al. |
| 5,507,795 A | 4/1996 | Chiang et al. |
| 5,514,115 A | 5/1996 | Frantzen et al. |
| 5,527,325 A | 6/1996 | Conley et al. |
| 5,549,601 A | 8/1996 | McIntyre et al. |
| 5,569,277 A | 10/1996 | Evans et al. |
| 5,571,122 A | 11/1996 | Kelly et al. |
| 5,571,130 A | 11/1996 | Simpson et al. |
| 5,584,842 A | 12/1996 | Fogarty et al. |
| 5,620,447 A | 4/1997 | Smith et al. |
| 5,624,457 A | 4/1997 | Farley et al. |
| 5,632,754 A | 5/1997 | Farley et al. |
| 5,634,464 A | 6/1997 | Jang et al. |
| 5,643,296 A | 7/1997 | Hundertmark et al. |
| 5,643,298 A | 7/1997 | Nordgren et al. |
| 5,665,098 A | 9/1997 | Kelly et al. |
| 5,669,920 A | 9/1997 | Conley et al. |
| 5,674,232 A | 10/1997 | Halliburton |
| 5,695,506 A | 12/1997 | Pike et al. |
| 5,700,687 A | 12/1997 | Finn |
| 5,709,698 A | 1/1998 | Adams et al. |
| 5,733,296 A | 3/1998 | Rogers et al. |
| 5,741,270 A | 4/1998 | Hansen et al. |
| 5,776,114 A | 7/1998 | Frantzen et al. |
| 5,816,923 A | 10/1998 | Milo et al. |
| 5,836,957 A | 11/1998 | Schulz et al. |
| 5,843,103 A | 12/1998 | Wulfman |
| 5,868,685 A | 2/1999 | Powell et al. |
| 5,868,767 A | 2/1999 | Farley et al. |
| 5,911,734 A | 6/1999 | Tsugita et al. |
| 5,916,210 A | 6/1999 | Winston |
| 5,938,671 A | 8/1999 | Katoh et al. |
| 5,948,184 A | 9/1999 | Frantzen et al. |
| 5,951,482 A | 9/1999 | Winston et al. |
| 5,954,745 A | 9/1999 | Gertler et al. |
| 5,968,064 A | 10/1999 | Selmon et al. |
| 5,989,281 A | 11/1999 | Barbut et al. |
| 6,010,449 A | 1/2000 | Selmon et al. |
| 6,013,072 A | 1/2000 | Winston et al. |
| 6,022,362 A | 2/2000 | Lee et al. |
| 6,027,450 A | 2/2000 | Brown et al. |
| 6,027,514 A | 2/2000 | Stine et al. |
| 6,036,656 A | 3/2000 | Slater |
| 6,036,707 A | 3/2000 | Spaulding |
| 6,048,349 A | 4/2000 | Winston et al. |
| 6,063,093 A | 5/2000 | Winston et al. |
| 6,068,638 A | 5/2000 | Makower |
| 6,081,738 A | 6/2000 | Hinohara et al. |
| 6,106,515 A | 8/2000 | Winston et al. |
| 6,120,515 A | 9/2000 | Rogers et al. |
| 6,120,516 A | 9/2000 | Selmon et al. |
| 6,126,649 A | 10/2000 | VanTassel et al. |
| 6,134,033 A | 10/2000 | Bergano et al. |
| 6,157,852 A | 12/2000 | Selmon et al. |
| 6,159,225 A | 12/2000 | Makower |
| 6,183,432 B1 | 2/2001 | Milo |
| 6,190,353 B1 | 2/2001 | Makower et al. |
| 6,191,862 B1 | 2/2001 | Swanson et al. |
| 6,193,676 B1 | 2/2001 | Winston et al. |
| 6,217,527 B1 | 4/2001 | Selmon et al. |
| 6,217,549 B1 | 4/2001 | Selmon et al. |
| 6,221,049 B1 | 4/2001 | Selmon et al. |
| 6,228,076 B1 | 5/2001 | Winston et al. |
| 6,231,546 B1 | 5/2001 | Milo et al. |
| 6,231,549 B1 | 5/2001 | Noecker et al. |
| 6,235,000 B1 | 5/2001 | Milo et al. |
| 6,241,667 B1 | 6/2001 | Vetter et al. |
| 6,241,744 B1 | 6/2001 | Imran et al. |
| 6,258,052 B1 | 7/2001 | Milo |
| 6,266,550 B1 | 7/2001 | Selmon et al. |
| 6,283,951 B1 | 9/2001 | Flaherty et al. |
| 6,283,983 B1 | 9/2001 | Makower et al. |
| 6,299,622 B1 | 10/2001 | Snow et al. |
| 6,302,875 B1 | 10/2001 | Makower et al. |
| 6,330,884 B1 | 12/2001 | Kim |
| 6,355,005 B1 | 3/2002 | Powell et al. |
| 6,375,615 B1 | 4/2002 | Flaherty et al. |
| 6,394,976 B1 | 5/2002 | Winston et al. |
| 6,398,798 B2 | 6/2002 | Selmon et al. |
| 6,428,552 B1 | 8/2002 | Sparks |
| 6,443,966 B1 | 9/2002 | Shiu |
| 6,445,939 B1 | 9/2002 | Swanson et al. |
| 6,447,525 B2 | 9/2002 | Follmer et al. |
| 6,623,496 B2 | 9/2003 | Snow et al. |
| 6,638,233 B2 | 10/2003 | Corvi et al. |
| 2002/0022788 A1 | 2/2002 | Corvi et al. |
| 2002/0026103 A1* | 2/2002 | Norris et al. ............ 600/300 |
| 2002/0077642 A1 | 6/2002 | Patel et al. |
| 2003/0018346 A1 | 1/2003 | Follmer et al. |
| 2003/0120295 A1 | 6/2003 | Simpson et al. |
| 2003/0125757 A1 | 7/2003 | Patel et al. |
| 2003/0125758 A1 | 7/2003 | Simpson et al. |
| 2004/0167553 A1 | 8/2004 | Simpson |
| 2004/0167554 A1 | 8/2004 | Simpson |
| 2005/0154407 A1* | 7/2005 | Simpson ............... 606/159 |
| 2005/0177050 A1 | 8/2005 | Cohen |
| 2005/0177068 A1 | 8/2005 | Simpson |
| 2005/0222519 A1 | 10/2005 | Simpson |
| 2005/0222663 A1 | 10/2005 | Simpson et al. |
| 2006/0032508 A1 | 2/2006 | Simpson |
| 2006/0235366 A1 | 10/2006 | Simpson |
| 2006/0239982 A1 | 10/2006 | Simpson |
| 2007/0078469 A1 | 4/2007 | Soito et al. |
| 2008/0065124 A1 | 3/2008 | Olson |
| 2008/0065125 A1 | 3/2008 | Olson |

OTHER PUBLICATIONS

Ahn et al., "Status of Peripheral Atherectomy", Endovascular Surgery, Surgical Clinics of North America, vol. 72, No. 4, Aug. 1992, pp. 869-878.

Kuffer et al., "Simpson's Atherectomy of the Peripheral Arteries: Early Results and Follow-up", Rofo Fortschr Geb Rontgnestr Neuen Blidgeb Verfahr, Jul. 1990, vol. 153, No. 1, pp. 61-67.

Kuffer, "Peripheral Simpson Atherectomy. Indications and Results of a New Transluminal Procedure for Vascular Recanalization", Radiologe, Feb. 1990, vol. 30, No. 2, pp. 60-65.

Kuffer et al., "Secondary Simpson Atherectomy of Femoro-Popliteal Obstructions. Alternative or Supplementary Procedure to the Femoral Stent?", Vasa Suppl., 1992, vol. 35, pp. 187.

Kuffer et al., "Simpson's Atherectomy in Embolizing Leg Artery Stenoses", Rofo Fortschr Geb Rontgenstr Neuen Bildgeb Verfahr, Sep. 1991, vol. 155, No. 3, pp. 235-241.

Steckmeier et al., "Experiences with Rotation Atherectomy and Atherectomy", Herz, Feb. 1989, vol. 14, No. 1, pp. 43-51.

Di Sciascio et al., "Directional Coronary Atherectomy: From Therapeutic Device to Research Tool in Coronary Artery Disease", Cardiologia, Apr. 1999, vol. 44, No. 4, pp. 333-339.

Ikeno et al., "Early Experience With a Novel Plaque Excision System for the Treatment of Complex Coronary Lesions", Catheterization and Cardiovascular Interventions, 2004, vol. 61, pp. 35-43.

Cook et al., "DNA Microarrays: Implications for Cadriovascular Medicine", Circulation Research, 2002, vol. 91, pp. 559-564.

Patino et al., "Serial Analysis of Gene Expression: Technical Considerations and Applications to Cardiovascular Biology", Circulation Research, 2002, vol. 91, pp. 565-569.

Levy et al., "Microarray Analysis of Neointima: Flowing Toward a Clear Future", Arterioscler Thromb Vasc Biol., 2002, vol. 22, pp. 1946-1947.

Ye et al., "Microarray, SAGE and their Applications to Cardiovascular Diseases", Cell Research, 2002, vol. 12, No. 2, pp. 105-115.

Gonschior et al., "Results of Directional Peripheral Atherectomy with Reference to Histology, Histochemistry, and Ultrastructure", The Journal of Vascular Diseases, Jun. 1993, pp. 454-463.

Johnson et al., "Primary Peripheral Arterial Stenoses and Restenoses Excised by Transluminal Atherectomy: A Histopathologic Study", J Am Coll Cardiol, Feb. 1990, vol. 15, No. 2, pp. 419-425.

Waller et al., "Histologic Analysis of Directional Coronary Atherectomy Samples: A Review of Findings and their Clinical Relevance", The American Journal of Cardiology, Oct. 18, 1993, vol. 72, pp. 80E-87E.

DiSciascio et al., "Histopathologic Correlates of Unstable Ischemic Syndromes in Patients Undergoing Directional Coronary Atherectomy: In Vivo Evidence of Thrombosis, Ulceration, and Inflammation", Am Heart J., Sep. 1994, vol. 128, No. 3, pp. 419-426.

Krings et al., "Ultrastructural and Proliferation Studies of Human, Catheter Atherectomy Extracted Plaque Material", Vasa Suppl., 1991, vol. 33, pp. 149-150.

Bauriedel et al., "Cellularity and Ultrastructural Characteristics of Human Atherectomy Specimens: Comparison Between Resenosis and Primary Stenotic of Coronary and Peripheral Lesions", Z Kardiol., Aug. 1993, vol. 82, No. 8, pp. 485-493.

Hofling et al., "Analysis of Atherectomy Specimens", Am J Cardiol, Oct. 18, 1993, vol. 72, No. 13, pp. 96E-107E.

MacLeod et al., "Proliferation and Extracellular Matrix Synthesis of Smooth Muscles Cultured From Human Coronary Atherosclerotic and Restenotic Lesions", J Am Coll Cardiol., Jan. 1994, vol. 23, No. 1, pp. 59-65.

Hanke et al, "Accumulation of Macrophages in the Arterial Vessel Wall Following Experimental Balloon Angioplasty", Eur Heart J, May 1994, vol. 15, No. 5, pp. 691-698.

Zohlnhöfer et al., "Gene Expression Profiling of Human Stent-Induced Neointima by cDNA Array Analysis of Microscopic Specimens Retrieved by Helix Cutter Atherectomy", Circulation, 2001, vol. 103, pp. 1396-1402.

Williams et al., "Directional Coronary Atherectomy: But Wait, There's More", Circulation, 1998, vol. 97, pp. 309-311.

Hofling et al., "Angiography and Functional Results and Histologic Findings Following Percutaneous Atherectomy in Patients with Arterial Occlusive Disease", Z Kardiol, Sep. 1989, vol. 78, No. 9, pp. 561-566.

Grant et al., "Expression of IGF-I, IGF-I Receptor and IGF Binding Proteins-1, -2, -3, -4 and -5 in Human Atherectomy Specimens", Regul Pept., Dec. 17, 1996, vol. 67, No. 3, pp. 137-144.

Taylor et al., "Proliferative Activity in Coronary Atherectomy Tissue. Clinical, Histopathologic, and Immunohistochemical Correlates", Chest, Sep. 1995, vol. 108, No. 3, pp. 815-820.

Yutani et al., "Histologic Evidence of Foreign Body Granulation Tissue and De Novo Lesions in Patients with Coronary Stent Restenosis", Cardiology, 1999, vol. 92, No. 3, pp. 171-177.

Veinot et al., "Preliminary Clinical Experience with the Pullback Atherectomy Catheter and the Study of Proliferation in Coronary Plaques", Can J Cardiol, Dec. 1998, vol. 14, No. 12, pp. 1457-1463.

Arbustini et al., "Histopathologic Features in Atherectomy Samples Obtained From Patient with Unstable Angina, Stable Angina and Restenosis. Direct Atherectomy Lombardi Group", G Ital Cardiol., Jun. 1996, vol. 26, No. 6, pp. 623-633.

Ellis et al., "Relation of Clinical Presentation, Stenosis Morphology, and Operation Technique to the Procedural Results of Rotational Atherectomy and Rotational Atherectomy-Facilitated Angioplasty", Circulation, Feb. 1994, vol. 89, No. 2, pp. 882-892.

Ellis et al., "Relation of Stenosis Morphology and Clinical Presentation to the Procedural Results of Directional Coronary Atherectomy", Circulation, Aug. 1991, vol. 84, No. 2, pp. 644-653.

Dartsch et al., "Cell Constitution and Characteristics of Human Atherosclerotic Plaque Selectively Removed by Percutaneous Atherectomy", Atherosclerosis, Dec. 1989, vol. 80, No. 2, pp. 149-157.

Ballantyne, et al., "Markers of Inflammation and Their Clinical Significance", *Athero Supp.* 6:21-29.

Ballantyne, et al., "Lipoprotein-Associated Phospholipase $A_2$, High-Sensitivity C-Reactive Protein, and Risk for Incident Coronary Heart Disease in Middle-Aged Men and Women in the Atherosclerosis Risk in Communities (ARIC) Study", *Circulation* 109:837-842 (2004).

Brilakis, et al., "Association of lipoprotein-associated phospholipase A2 levels with coronary artery disease risk factors, angiographic coronary artery disease, and major adverse events at follow-up", *European Heart Journal* 26(2):137-144 (2005).

Cipollone, et al., "High preprocedural non-HDL cholesterol is associated with enhanced oxidative stress and monocyte activation after coronary angioplasty: possible implications in restenosis" *Heart* 89:773-779 (2003).

Hojo, et al., "Matrix metalloproteinase expression in the coronary circulation induced by coronary angioplasty" *Atherosclerosis* 161:185-193 (2002).

Hojo, et al., "Chemokine expression in coronary circulation after coronary angioplasty as a prognostic factor for restenosis" *Atherosclerosis* 156:165-170 (2001).

Hojo, et al., "Interleukin 6 expression in coronary circulation after coronary angioplasty as a risk factor for Restenosis" *Heart* 84:83-87 (2000).

Horie, et al., "Association of an Acute Reduction in Lipoprotein(a) With Coronary Artery Restenosis After Percutaneous Transluminal Coronary Angioplasty" *Circulation* 96(1):166-173 (1997).

Inoue, et al., "Expression of Polymorphonuclear Leukocyte Adhesion Molecules and Its Clinical Significance in Patients Treated with Percutaneous Transluminal Coronary Angioplasty" *JACC* 28(5):1127-1133 (1996).

Kurz, et al., "Increased serum concentrations of adhesion molecules after coronary angioplasty" *Clinical Science* 87:627-633 (1994).

Mukherjee, et al., "Elective coronary revascularization, an iatrogenic form of acute coronary syndrome: How can clinicians reduce the risk?", *American Heart Journal* 148(3):371-377 (2004).

Tashiro, et al., "Role of cytokines in the pathogenesis of restenosis after percutaneous transluminal coronary angioplasty" *Coronary Artery Disease* 12(2):107-113 (2001).

Winkler, et al., "Platelet-Activating Factor Acetylhydrolase Activity Indicates Angiographic Coronary Artery Disease Independently of Systemic Inflammation and Other Risk Factors" *Circulation* 111:980-987 (2005).

Supplementary European Search Report dated Dec. 9, 2009, issued in connection with counterpart European patent application No. 06825062.0.

* cited by examiner

LIBRARIES AND DATA STRUCTURES OF MATERIALS REMOVED BY DEBULKING CATHETERS

CROSS-REFERENCES TO RELATED APPLICATIONS

The present application is a continuation-in-part of U.S. patent application Ser. No. 11/108,887, filed Apr. 19, 2005. The complete disclosure of which is incorporated herein by reference.

TECHNICAL FIELD OF THE INVENTION

The present invention relates generally to computer readable media for storing data relating to patients and tissue samples excised from their vascular or other lumens. The data may be used to analyze current, past, or future patient health, to assess treatments, to evaluate drugs, to evaluate risk factors, and to determine proposed treatments or assessments.

BACKGROUND OF THE INVENTION

Cardiovascular disease frequently arises from the accumulation of atheromatous material on the inner walls of vascular lumens, particularly arterial lumens of the coronary and other vasculature, resulting in a condition known as atherosclerosis. Atherosclerosis occurs naturally as a result of aging, but may also be aggravated by factors such as diet, hypertension, heredity, vascular injury, and the like. Atheromatous and other vascular deposits restrict blood flow and can cause ischemia which, in acute cases, can result in myocardial infarction. Atheromatous deposits can have widely varying properties, with some deposits being relatively soft and others being fibrous and/or calcified. In the latter case, the deposits are frequently referred to as plaque.

One conventional treatment for cardiovascular disease is the use of stents. Endoluminal stents are commonly used to treat obstructed or weakened body lumens, such as blood vessels and other vascular lumens. Once deployed in the blood vessel, the stent can remain in the body lumen where it will maintain the patency of the lumen and/or support the walls of the lumen which surround it. One factor impeding the success of stent technology in endoluminal treatments is the frequent occurrence of in-stent restenosis, characterized by proliferation and migration of smooth muscle cells within and/or adjacent to the implanted stent, causing reclosure or blockage of the body lumen.

Atherosclerosis and restenosis can be treated in a variety of ways, including drugs, bypass surgery, and a variety of catheter-based approaches which rely on intravascular debulking or removal of the atheromatous or other material occluding a blood vessel. Of particular interest to the present invention, a variety of methods for cutting or dislodging material and removing such material from the blood vessel have been proposed, generally being referred to as atherectomy procedures. Atherectomy catheters intended to excise material from the blood vessel lumen generally employ a rotatable and/or axially translatable cutting blade which can be advanced into or past the occlusive material in order to cut and separate such material from the blood vessel lumen.

There is a need in the art for methods and tools for managing and storing materials removed from body lumens. There is a need in the art for methods and tools for managing and storing information related to and/or derived from materials removed from body lumens.

BRIEF SUMMARY OF THE INVENTION

One aspect of the invention provides one or more computer readable media having a data structure stored thereon. The data structure comprises a first data field comprising a value corresponding to a property of a first tissue sample excised from a vascular lumen of a patient and a second data field comprising data identifying the patient. Optional additional data fields include a third data field comprising a value corresponding to cardiac health of the patient, a fourth data field comprising a value corresponding to a characteristic of the patient's blood, a fifth data field comprising a value corresponding to family history of the patient, a sixth data field comprising a value corresponding to the patient's medical history, a seventh data field comprising a value corresponding to a property of a second tissue sample excised from a vascular lumen of the patient at a distinct time, an eighth data field comprising a value corresponding to a property of a second tissue sample excised from distinct vascular lumen of the patient on the same day as the first tissue sample, a ninth data field which comprises a value which links a labeled storage container comprising excised tissue with a value in the second data field, a tenth data field which comprises a value which links the labeled storage containers comprising a component extracted or processed from an extracted tissue with a value in the second data field. These can be used separately or cumulatively. These data fields are not an exclusive list of possible useful data fields.

For a further understanding of the nature and advantages of the invention, reference should be made to the following description.

DETAILED DESCRIPTION OF THE INVENTION

Data collected related to samples of materials removed from body lumens can be stored in data structures. The stored data can be used to draw correlations, to stratify groups of patients, to provide risk assessments, to provide diagnoses and/or prognoses. Libraries of samples can be assembled to be used for studies of drugs, candidate drugs, toxins, therapeutic treatments, etc. The samples can be preserved according to any method known in the art. Samples may be frozen, for example, in liquid nitrogen. They may be preserved in paraffin, dried, freeze dried, etc. Samples may be treated to achieve a purified or semi-purified component of the sample. Samples may be treated, for example to extract DNA or protein. Samples may be treated to extract mRNA and to preserve it or "convert" it to cDNA. Desirably, samples are stored in a consistent and systematic way so that patient information remains associated with the samples so that patient outcome or other data collected at a later time can be associated with the sample concurrently or at a later time.

Samples within a library can be stored and associated with information related to the sample itself, e.g., its properties, and the patient from whom the sample was excised. Other information that can be associated with the sample include results of analyses of the sample, patient history information, patient outcome information, drug efficacy information, therapeutic efficacy information, family history, factors of the patient related to cardiac disease, factors of the patient related to non-cardiac disease. In some cases this information may be stored without association with the physical samples. Patient identifying information may be coded so that confidentiality can be maintained while still permitting correlation of various patient attributes with the samples.

One or more aspects of the invention may be embodied in computer-usable data and computer-executable instructions, such as in one or more program modules, executed by one or more computers or other devices. Generally, program modules include routines, programs, objects, components, data structures, etc. that perform particular tasks or implement particular abstract data types when executed by a processor in a computer or other device. The computer executable instructions may be stored on a computer readable medium such as a hard disk, optical disk, removable storage media, solid state memory, RAM, etc. As will be appreciated by one of skill in the art, the functionality of the program modules may be combined or distributed as desired in various catheters. In addition, the functionality may be embodied in whole or in part in firmware or hardware equivalents such as integrated circuits, field programmable gate arrays (FPGA), and the like. Particular data structures may be used to more effectively implement one or more aspects of the invention, and such data structures are contemplated within the scope of computer executable instructions and computer-usable data described herein.

Data fields which are present in the data structures of the present invention may include one or more of those discussed below. A first data field comprises a value corresponding to a property of a first tissue sample excised from a vascular lumen of a patient. The tissue sample is typically material that has been excised from a body lumen. The body lumen is often a vascular lumen. The property may be, for example, level of a marker in the tissue, composition of the tissue sample, histologic characterization, immunochemical characterization of the tissue, a genomic characteristic of the tissue, level of a mRNA in the tissue, location of the vascular lumen from which the tissue was excised, or volume or mass of the excised tissue. Any property of the tissue may be stored in this data field. A second data field may comprise data identifying a patient. The patient data may be anonymous or identify a person. If anonymous, the code will uniquely identify a patient's characteristics, without actually identifying the patient. Thus data can be used for studies, without divulging identities of the patients.

An optional third data field comprises a value corresponding to cardiac health of the patient. Such values may, for example, relate to past infarct history, past angioplasty procedures, or past cholesterol values. A possible fourth data field comprises a value corresponding to a characteristic of the patient's blood. The blood may have been withdrawn at the time of or before tissue excision. The blood characteristic may be any known in the art, including but not limited to, sedimentation rate, red blood cell count, white blood cell count, triglycerides, and C-reactive protein.

An optional fifth data field comprises a value corresponding to family history of the patient. Thus a value can be assigned to family history events based on degree of relatedness of the family member and the severity of the event. An optional sixth data field comprises a value corresponding to the patient's own medical history. This history includes but is not limited to cardiac related events. Thus other medical history events can be recorded which may not be currently known to be associated with vascular occlusion, but which may in fact have a correlation. Such data will make the data structure useful for discovering new associations, risks, and mechanisms. Such data may also be useful in stratifying patients for treatment regimens and for drug trials.

An optional seventh data field comprises a value corresponding to a property of a second tissue sample excised from a vascular lumen of the patient at a distinct time from the first tissue sample. The second tissue sample can be excised from the same vascular lumen as the first tissue sample or from a different vascular lumen of the patient. An optional eighth data field comprises a value corresponding to a property of a second tissue sample excised from a distinct vascular lumen of the patient on the same day as the first tissue sample.

The computer readable media can optionally be associated with one or more excised tissue samples in labeled storage containers. Labeled storage containers includes storage containers that are in fixed positions or parts of a machine or apparatus which positions are themselves labeled. If such stored tissue samples are associated with the data structure, an optional ninth data field can be used which comprises a value which links the labeled storage containers with a value in the second data field. Alternatively, the labeled storage containers may be labeled with a value in the second data field. Alternatively or optionally the data structure can be associated with labeled storage containers in which one or more samples comprise a component extracted or processed from an excised vascular tissue from a vascular lumen of the patient. Such components include DNA, RNA, cDNA, lipid, carbohydrate, and protein. In such a case, the data structure can optionally comprise a tenth data field in which a value which links the labeled storage containers with a value in the second data field is present. Alternatively, such labeled storage containers can be labeled with a value in the second data field. There is no significance to the numbers of the data fields as used herein. Data fields with sequential numbers need not be used. Thus, for example, a structure can comprise data fields with fields 1, 2, 5, and 6 without data fields 3, 4, 7, 8, 9, and 10.

Catheters can be used to debulk atheroma and other occlusive material from diseased body lumens, and in particular coronary arteries, de novo lesions, and in-stent restenosis lesions. Catheters are also suitable for treating stenoses of body lumens and other hyperplastic and neoplastic conditions in other body lumens, such as the ureter, the biliary duct, respiratory passages, the pancreatic duct, the lymphatic duct, and the like. Neoplastic cell growth will often occur as a result of a tumor surrounding and intruding into a body lumen. Debulking of such material can thus be beneficial to maintain patency of the body lumen. The debulked material is typically a continuous strip of tissue removed from the lumen interior wall that ranges from about 1 mg to about 2000 mg; it retains the structure of the tissue prior to removal. The continuous strip or strand of tissue removed will typically have a length that is longer than a length of the cutting window. The data storage and access structures of the present invention can be applied to a variety of occlusive, stenotic, or hyperplastic material in a variety of body lumens.

Apparati will generally comprise catheters having catheter bodies adapted for intraluminal introduction to the target body lumen. The dimensions and other physical characteristics of the catheter bodies will vary significantly depending on the body lumen which is to be accessed. In the exemplary case of atherectomy catheters intended for intravascular introduction, the proximal portions of the catheter bodies will typically be very flexible and suitable for introduction over a guidewire to a target site within the vasculature.

Generally, the smooth muscle cells of the stenotic material show a range of phenotypes, but most of the cells contained myofilaments as well as a relatively high amount of synthetic organelles, such as rough endoplasmic reticulum, Golgi apparatus and mitochondria. One can determine how much stenotic tissue is retrieved in an access procedure. One can determine presence or absence of inflammatory cells in excised tissue. One can determine the presence of inflammatory cells within critical areas of plaque. Determination of the location and degree of inflammatory cells present may facilitate a more informed characterization or diagnosis.

The material removed from a catheter collection chamber, or a portion thereof, can be placed in a preserving agent, a tissue fixative, and or a preparation agent suitable for a desired test prior to testing the material. The material removed from the patient by this method is typically at least one or more continuous strip(s) of material that maintains the structure of the material in vivo. The quantity of material removed by the method can be from about 1 mg to about 2000 mg. Typically the amount of material is about 1 mg to about 100 mg, about 100 mg to about 200 mg, about 200 mg to about 300 mg, 300 mg to about 400 mg, 400 mg to about 500 mg, 500 mg to about 600 mg, about 600 mg to about 700 mg, 700 mg to about 800 mg, or about 800 mg to about 2000 mg. In a typical procedure about 400 mg to about 600 mg of material is removed and available for testing and/or storage. Collection of one or more continuous strips of material from the inner surface of a lumen may be longer than a largest dimension of the cutting window of a catheter used to remove the material. In a particular example, the material can comprise plaque tissue. The material can be collected from a single site or at least one additional site in the same or a different body lumen.

Excised material can be stored to permit later confirmatory or additional testing without having to subject the patient to another percutaneous translumenal lumenectomy procedure. The material can be tested by genomic screening, DNA hybridization, RNA hybridization, gene expression analysis, PCR amplification, proteomic testing, drug efficacy screening, presence of one or more protein markers, presence of one or more DNA markers, presence of one or more RNA markers, histological testing, histopathology, cytopathology, cell and tissue type analysis, biopsy, and the like. Additionally, the material can also be cultured and/or tested to determine sensitivity to drugs, toxins, and the like. The material can be tested for the presence of DNA, RNA, or protein markers comprising a smooth muscle proliferative promoter, a smooth muscle proliferative inhibitor, a cellular marker, an apoptotic marker, a cell cycle protein, a transcriptional factor, a proliferative marker, an endothelial growth factor, an adhesion molecule, a cytokine, a chemokine, a chemokine receptor, an inflammation marker, a coagulation factor, a fibrinolytic factor, an oxidative stress related molecule, an extracellular matrix molecule, an interleukin, a growth factor, a glycoprotein, a proteoglycan, a cell-surface marker, a serum marker, and or an immune factor, and the like. Tests for each of these molecules and others are well known to the skilled artisan as are methods and preservatives, fixatives and preparation agents for adding to all or a portion of the material collected. The results of any of the tests for properties of the removed material can be stored in a data structure according to the invention.

The material produced by a lumenectomy comprises at least one continuous tissue stand collected in vivo from an inner surface of the body lumen of a subject. The body lumen can be an artery or other lumen or vessel of the circulatory system and the material can comprise arterial plaque and associated tissue. The continuous strand of tissue provided by the disclosed methods provide a sufficient amount of high quality material to successfully perform at least one or more tests comprising, for example, genomic screening, DNA hybridization, RNA hybridization, gene expression analysis (including serial analysis of gene expression), PCR amplification, proteomic testing, drug efficacy screening, a determination of the presence of one or more protein markers, a determination of the presence of one or more DNA markers, a determination of the presence of one or more RNA markers, histological testing, histopathology, cytopathology, cell type analysis, tissue type analysis, biopsy, and the like. Methods for performing each of the tests are well known to the skilled artisan. It is also well known that material collected from a patient can be added to a preserving agent, tissue fixative, or a preparation agent in order to prepare at least a portion of collected material for the desired test. Agents known in the art for preserving, fixing or preparing the material for later use include, for example, saline, heparinized saline, liquid nitrogen, formalin, a membrane lysis agent, a RNA or DNA preparation agent, and the like. Particular tests that can be carried out successfully on the excised lumenectomy material include, but are not limited to, histology techniques including hematoxylin and eosin staining, connective tissue staining, carbohydrate staining, and lipid staining, and the like. In addition, tissue array testing, enzyme histochemistry, transmission electron microscopy, immunohistology, immunocytochemistry, immunoassays, immunofluorescent assays, immunoprecipitation assays, ELISA, flow cytometry, fluorescent activated cell sorting, radioimmunochemistry, electrophoresis, two-dimensional gel electrophoresis, Western blotting, protein sequencing, mass spectrometry, proteomic analysis, and protein microarray analysis can be carried out. Further, cytogenetic testing, Nothern blotting, RNase protection assays, in situ hybridization assays, DNA microarray testing, reverse transcription polymerase chain reaction PCR (RT-PCR), Southern blotting, DNA sequencing, PCR amplification, single strand conformational polymorphism assays, single strand polymorphism (SNP) assays, and serial analysis of gene expression (SAGE) assays can be successfully carried out with the lumenectomy materials compositions. The compositions can also be prepared for storage for later testing.

Table 1 shows relevant markers for which the excised vascular material can be tested for expression, and about which data can be stored.

The material collected can be analyzed for the presence of DNA, RNA, or protein markers comprising smooth muscle proliferative promoters (platelet-derived growth factor (PDGF), and PDGF receptor), basic fibroblast growth factor (FGF) and FGF receptor, interleukin 1 (IL-1), or transforming growth factor α (TGFα), and the like), smooth muscle proliferative inhibitors (nitric oxide/endothelial-derived relaxing factors (NO/EDRF), interferon γ (IFγ), transforming growth factor β (TGFβ), or TGFβ receptor, and the like), cellular markers (including CD68, CD3, CD4, CD8, CD20, smooth muscle actin, or CD31, and the like), apoptotic markers (Bcl-x, Bcl-2, Bax, Bak, or P53, and the like), cell cycle proteins (cyclin A, cyclin B, cyclin D, or cyclin E, and the like), transcriptional factors (transcription factor NFκB, transcription factor E2F, transcription factor CREB, or transcription factor KLF5/BTEB2, and the like), proliferative markers (Ki-67 or proliferating cell nuclear antigen (PCNA), and the like), endothelial growth factors (vascular endothelial growth factor (VEGF), and the like), adhesion molecules (intercellular adhesion molecule-1 (ICAM-1), CD11a/CD18 (LFA-1), CD11b/CD18 (MAC-1), vascular cell adhesion molecule-1 (VCAM-1), p-selectin (CD62P), or integrin, and the like), cytokines (interleukin 6 (IL-6) or interleukin 8 (IL-8), and the like), chemokines and chemokine receptors (monocyte chemoattractant protein 1 (MCP-1) and its receptor CCR2, CX3C chemokine fractalkine and its receptor CX3CR1, or eotaxin and its receptor CCR3, and the like), inflammation markers (C-reactive protein, myeloperoxidase, or complement proteins, and the like), coagulation factors and fibrinolytic factors (fibrinogen, prothrombinogen, plasminogen activator, tissue factor, or glycoprotein receptor on platelets (GpIIb-IIIa), and the like), oxidative stress related molecules (oxidized LDL and its receptor CD36, or lipoxygenase, and the like), extracellular matrix molecules (collagen, matrix metalloproteinase (MMP), FK506-binding protein 12 (FKBP12), endothelial differentiation gene receptors (EDG receptors), ephrins, elastin, lamin receptor, monocyte colony stimulating factor (M-CSF), tumor necrosis factor (TNF), or PDZ domain proteins, and the like), interleukins (interleukin 1 (IL-1), interleukin 6 (IL-6), or interleukin 8 (IL-8), and the like), growth factors (platelet-derived frowth factor (PDGF), basic fibroblast growth factor (FGF), transforming growth factor α (TGFα), or transforming growth factor β (TGFβ), and the like), glycoproteins, proteoglycans (versican, hyluronan, biglycan, or deorin, and the like), cell-surface markers, serum markers, and/or immune factors (stromal cell-derived factor 1a (SDF-1)), and the like). Analysis of the excised material by any of the above tests can be used for diagnosis of a condition in a patient, to design a treatment directive or protocol for a subject, to monitor progress of a treatment regimen, or if tests from a number of individuals are compared, the information can be used in a multi-patient analysis, such as a cardiovascular disease population study.

While all the above is a complete description of the preferred embodiments of the inventions, various alternatives, modifications, and equivalents may be used. Therefore, although the foregoing invention has been described in detail for purposes of clarity of understanding, it will be obvious that certain modifications may be practiced within the scope of the appended claims.

What is claimed is:

1. An article of manufacture, said article comprising:
   a computer readable media having computer executable instructions stored thereon, which when executed by a computer causes the computer to perform an operation comprising:
   receiving a plurality of sets of data fields derived from patient samples, wherein each set of data fields comprise:
      a first value corresponding to a property of a first excised tissue sample comprising one or more continuous strips of material from the inner surface of a vascular lumen, and
      a second value corresponding to data identifying a patient;
      a third data field corresponding to the patient's health;
      storing the plurality of sets of data fields;
      correlating the data fields; and
      stratifying the patient for a treatment regime.

2. The article of manufacture of claim 1 wherein the third data field comprises a value corresponding to cardiac health of the patient.

3. The article of manufacture of claim 1 wherein the property is selected from the group consisting of: a level of a marker in the tissue, a composition of the tissue sample, histologic characterization of the tissue, an immunochemical characterization of the tissue, a genomic characteristic, level of a mRNA, a location of the vascular lumen from which the tissue was excised, a volume or a mass of the excised tissue.

4. The article of manufacture of claim 1 further comprising: a fourth data field comprising a value corresponding to a characteristic of the patient's blood.

5. The article of manufacture of claim 4 wherein the patient's blood was withdrawn at the time of or before tissue excision.

6. The article of manufacture of claim 1 further comprising: a fifth data field comprising a value corresponding to family history of the patient.

7. The article of manufacture of claim 1 further comprising: a sixth data field comprising a value corresponding to the patient's medical history.

8. The article of manufacture of claim 1 further comprising: a seventh data field comprising a value corresponding to a property of a second tissue sample excised from the vascular lumen of the patient at a distinct time.

9. The article of manufacture of claim 8 wherein the second tissue sample is excised from the same vascular lumen as the first tissue sample.

10. The article of manufacture of claim 1 further comprising: an eighth data field comprising a value corresponding to a property of a second tissue sample excised from distinct vascular lumen of the patient on a same day as the first tissue sample.

11. The article of manufacture media of claim 1 wherein said media are associated with one or more excised tissue samples in labeled storage containers, wherein the computer readable media comprise a ninth data field which comprises a value which links the labeled storage containers with a value in the second data field.

12. The article of manufacture of claim 1 wherein said media are associated with one or more excised tissue samples in labeled storage containers, wherein the storage containers are labeled with a value in the second data field.

13. The article of manufacture of claim 1 wherein said media are associated with one or more samples in labeled storage containers, wherein the one or more samples comprise a component extracted or processed from an excised vascular tissue from a vascular lumen of the patient, wherein the component is selected from the group consisting of DNA, RNA, cDNA, and protein, and wherein the computer readable media comprise a tenth data field which comprises a value which links the labeled storage containers with a value in the second data field.

14. The article of manufacture of claim 1 wherein said media are associated with one or more samples in labeled storage containers, wherein the storage containers are labeled with a value in the second data field, wherein the samples comprise a component extracted or processed from an excised vascular tissue from a vascular lumen of the patient, wherein the component is selected from the group consisting of DNA, RNA, cDNA, and protein.

15. The article of manufacture of claim 1 wherein said vascular lumen comprises an artery and said tissue sample comprises a member selected from the group consisting of a plaque, an occlusive material, a stenotic material, and a hyperplastic material.

16. The article of manufacture of claim 15 wherein said value comprises a result of a characterization, a test, or a diagnosis performed on said first excised tissue sample, which result is stored within said first data structure.

17. The article of manufacture of claim 16 wherein said result comprises therapeutic efficacy information.

18. The article of manufacture of claim 17 wherein said therapeutic efficacy information comprises an efficacy of a treatment or a drug.

19. The article of manufacture of claim 16 wherein said test comprises a member selected from the group consisting of: a genomic screening, a DNA hybridization, a RNA hybridization, a gene expression analysis, a PCR amplification, a proteomic test, a drug efficacy screening, a determination of the presence of one or more protein markers, a determination of the presence of one or more DNA markers, a determination of the presence of one or more RNA markers, a histological test, a histopathology, a cytopathology, a cell type analysis, a tissue type analysis, a test to determine sensitivity to drugs, a test to determine sensitivity to toxins, and a biopsy.

* * * * *

UNITED STATES PATENT AND TRADEMARK OFFICE
CERTIFICATE OF CORRECTION

PATENT NO.         : 7,794,413 B2
APPLICATION NO.    : 11/230924
DATED              : September 14, 2010
INVENTOR(S)        : Angela Soito and John B. Simpson It is certified that error appears in the above-identified patent and that said Letters Patent is hereby corrected as shown below:

Insert the following table after col. 7, line 27:

--Table 1

Markers upregulated in vascular disease

```
AA775616 osteopontin
AA682386 oxidised low density lipoprotein (lectin-like) receptor 1
AA969504 interferon, gamma
AA102526 interleukin 8
BU631490 tissue inhibitor of metalloproteinase 2
NM_002356 myristoylated alanine-rich protein kinase C substrate
NM_000930 plasminogen activator, tissue
NM_002117 major histocompatibility complex, class I, C
AI129421 interleukin 18 (interferon-gamma-inducing factor)
W51794  matrix metalloproteinase 3 (stromelysin 1, progelatinase)
AA143201 matrix metalloproteinase 1 (interstitial collagenase)
N94616 laminin, alpha 4
NM_021999 integral membrane protein 2B
NM_000584 interleukin 8
NM_002510 glycoprotein (transmembrane) nmb
N53447 integral membrane protein 2A
NM_002659 plasminogen activator, urokinase receptor
AL133111 SH3-domain binding protein 5 (BTK-associated)
NM_147780 cathepsin B
W46577 endothelial cell-specific molecule 1
```

Signed and Sealed this
Thirtieth Day of October, 2012

David J. Kappos
*Director of the United States Patent and Trademark Office*

AA857496 matrix metalloproteinase 10 (stromelysin 2)
NM_005502 ATP-binding cassette, sub-family A (ABC1), member 1
AI342012 macrophage scavenger receptor 1
AA490846 integrin, alpha 4 (antigen CD49D, alpha 4 subunit of VLA-4 receptor)
AA454999 hypothetical protein FLJ10111
AK093984 hypothetical protein MGC5618
AA666269 integrin, beta 3 (platelet glycoprotein IIIa, antigen CD61)
NM_005625 syndecan binding protein (syntenin)
BC014989 phospholipid scramblase 3
AI279830 protein phosphatase 1, regulatory (inhibitor) subunit 16B
AA936768 interleukin 1, alpha
NM_001920 decorin
AK055130 calmodulin 2 (phosphorylase kinase, delta)
NM_016497 mitochondrial ribosomal protein L51
AA451863 CD4 antigen (p55)
NM_058197 cyclin-dependent kinase inhibitor 2A
R10284 hyaluronan-mediated motility receptor (RHAMM)
AI309439 integrin, alpha M (complement component receptor 3, alpha)
AI334914 integrin, alpha 2b
AF001893 multiple endocrine neoplasia I
N36136 endomucin-2
AW772163 hypothetical protein FLJ20401
NM_001964 early growth response 1
AA454668 prostaglandin-endoperoxide synthase 1
NM_004530 matrix metalloproteinase 2
AK027663 stanniocalcin 2
AA057204 interleukin 2 receptor, beta
NM_001444 fatty acid binding protein 5 (psoriasis-associated)
AA873792 small inducible cytokine A5 (RANTES)

Markers upregulated in diabetes

AA936768 interleukin 1, alpha
NM_000600 interleukin 6 (interferon, beta 2)
N98591 interleukin 6 (interferon, beta 2)
AA156031 metallothionein 2A
NM_001235 serine (or cysteine) proteinase inhibitor, clade H
BF131637 metallothionein 2A
NM_006216 serine (or cysteine) proteinase inhibitor, clade E
NM_001552 insulin-like growth factor binding protein 4
NM_004530 matrix metalloproteinase 2
NM_000088 collagen, type I, alpha 1
NM_023009 MARCKS-like protein
NM_003670 basic helix-loop-helix domain containing, class B, 2
T8095 Hs. clone 24707 mRNA sequence
NM_002993 chemokine C-X-C motif, granulocyte chemotactic protein 2
NM_006756 transcription elongation factor A (SII), 1
AI983239 Hs. cDNA FLJ32163 fis, clone PLACE6000371
NM_005110 glutamine-fructose-6-phosphate transaminase 2
NM_000584 interleukin 8
AK092836 Homo sapiens cDNA FLJ35517 fis, clone SPLEN2000698
NM_000104 cytochrome P450, subfamily I (dioxin-inducible), peptide
NM_004966 heterogeneous nuclear ribonucleoprotein F
AK025599 mannosidase, alpha, class 1A, member 1
NM_002923 regulator of G-protein signalling 2, 24kDa
AW005755 macrophage migration inhibitory factor
AA873792 small inducible cytokine A5 (RANTES)
U72621 pleiomorphic adenoma gene-like 1
NM_000358 transforming growth factor, beta-induced, 68kDa AK054688 Homo sapiens cDNA FLJ30126 fis, clone BRACE1000114
BC007583 Homo sapiens, clone MGC:15572 IMAGE:3140342
NM_000089 collagen, type I, alpha 2
NM_004404 neural precursor cell expressed, developmental regulated 5
NM_078467 cyclin-dependent kinase inhibitor 1A (p21, Cip1)
U97105 Homo sapiens N2A3 mRNA, complete cds
AI356451 CD19 antigen
BF732465 tissue inhibitor of metalloproteinase 2
NM_001554 cysteine-rich, angiogenic inducer, 61
BQ890604 Homo sapiens URB mRNA, complete cds
NM_002631 phosphogluconate dehydrogenase
N94503 pregnancy-associated plasma protein A
NM_001710 B-factor, properdin Markers upregulated in normal (non-diabetic) vessel segments NM_000584 interleukin 8
N98591 interleukin 6 (interferon, beta 2)
AA936768 interleukin 1, alpha
BM803108 ESTs
NM_000600 interleukin 6 (interferon, beta 2)
AI359876 EST
AA156031 metallothionein 2A
BF131637 metallothionein 2A
NM_003670 basic helix-loop-helix domain, class B, 2
NM_001235 serine (or cysteine) proteinase inhibitor, clade H
NM_004530 matrix metalloproteinase 2
NM_002982 monocyte chemotactic protein 1
NM_002631 phosphogluconate dehydrogenase NM_078467 cyclin-dependent kinase inhibitor 1A (p21, Cip1)
NM_152862 actin related protein 2/3 complex, subunit 2
NM_002923 regulator of G-protein signalling 2, 24kDa
AI983239 Hs. cDNA FLJ32163 fis, clone PLACE6000371
NM_005415 solute carrier family 20, member 1
AW772163 hypothetical protein FLJ20401
R21535 Hs. cDNA FLJ11724 fis, clone HEMBA1005331
NM_005110 glutamine-fructose-6-phosphate transaminase 2
AK092836 cDNA FLJ35517 fis, clone SPLEN2000698
NM_006216 serine (or cysteine) proteinase inhibitor, clade E Markers which are downregulated with statin treatment NM000600 interleukin 6 (interferon, beta 2)
N98591 interleukin 6 (interferon, beta 2)
NM_005746 pre-B-cell colony-enhancing factor
NM_ 002852 pentaxin-related gene, rapidly induced by IL-1 beta
N9201 fatty acid binding protein 4, adipocyte
NM_005110 glutamine-fructose-6-phosphate transaminase 2
AK094728 cDNA FLJ37409 fis, similar to COMPLEMENT C3
NM_004000 chitinase 3-like 2
NM_002923 regulator of G-protein signalling 2, 24kDa
T80495 Hs. clone 24707 mRNA sequence
AA936768 interleukin 1, alpha
NM_145791 microsomal glutathione-S-transferase 1
NM_006169 nicotinamide N-methyltransferase
AW007736 UDP-glucose ceramide glucosyltransferase
NM_005420 sulfotransferase, estrogen-preferring
NM_003670 basic helix-loop-helix domain containing, class B, 2

AA425102 monocyte chemotactic protein 1
NM_003254 tissue inhibitor of metalloproteinase 1
BF131637 metallothionein 2A
NM_000104 cytochrome P450, subfamily I (dioxin-inducible)
NM_001733 complement component 1, r subcomponent
NM_032849 hypothetical protein FLJ14834
NM_005328 hyaluronan synthase 2
NM_002009 fibroblast growth factor 7 (keratinocyte growth factor)
NM_002615 serine (or cysteine) proteinase inhibitor, clade F
NM_002658 plasminogen activator, urokinase
NM_033439 DVS27-related protein
AA381343 interleukin 6 (interferon, beta 2)
AW780123 ribosomal protein S26
M14219 chondroitin/dermatan sulfate proteoglycan (PG40) core
AF495759 Homo sapiens unknown mRNA
NM_001679 ATPase, Na+/K+ transporting, beta 3 polypeptide
NM_001029 ribosomal protein S26
NM_002074 guanine nucleotide binding protein, beta polypeptide 1
NM_001552 insulin-like growth factor binding protein 4
AF208043 interferon, gamma-inducible protein 16
AI268937 monocyte chemotactic protein 2
AA040170 monocyte chemotactic protein 3
AW131311 EST
NM_005415 solute carrier family 20 (phosphate transporter), member 1
NM_006988 a disintegrin-like and metalloprotease (reprolysin type)
NM_006307 sushi-repeat-containing protein, X chromosome
NM_000584 interleukin 8

D31887 KIAA0062 protein
NM_002229 jun B proto-oncogene
NM_002982 monocyte chemotactic protein 1

Markers downregulated with statin treatment

NM_002615 serine (or cysteine) proteinase inhibitor, clade F
AK094728 Homo sapiens cDNA FLJ37409 fis, clone BRAMY2028516
NM_001552 insulin-like growth factor binding protein 4
N92901 fatty acid binding protein 4, adipocyte
N98591 interleukin 6 (interferon, beta 2)
NM_000104 cytochrome P450, subfamily I (dioxin-inducible)
NM_006756 transcription elongation factor A (SII), 1
NM_000600 interleukin 6 (interferon, beta 2)
AF506819 Homo sapiens URB mRNA, complete cds
NM_145791 microsomal glutathione S-transferase 1
N39161 CD36 antigen (thrombospondin receptor)
M14219 Human chondroitin sulfate proteoglycan core protein
NM_031476 hypothetical protein DKFZp434B044
NM_000186 H factor 1 (complement)
NM_003254 tissue inhibitor of metalloproteinase 1
N98591 interleukin 6 (interferon, beta 2)
AJ318805 ESTs, Weakly similar to hypothetical protein FLJ20378
AA284954 colony stimulating factor 1 receptor
NM_002923 regulator of G-protein signalling 2, 24kDa
NM_001920 decorin
BI830199 likely ortholog of mouse Urb
AA451863 CD4 antigen (p55)

AA464526 interleukin 1 receptor, type I
AW192258 sprouty homolog 4 (Drosophila)
N68859 intercellular adhesion molecule 1 (CD54)
BC007552 Homo sapiens, clone MGC:15473 IMAGE:2967168, mRNA
NM_001733 complement component 1, r subcomponent
NM_006288 Thy-1 cell surface antigen
NM_000201 intercellular adhesion molecule 1 (CD54)
R22412 platelet/endothelial cell adhesion molecule (CD31 antigen)
NM_013417 isoleucine-tRNA synthetase
NM_004000 chitinase 3-like 2
R70506 growth factor receptor-bound protein 2
NM_030781 collectin sub-family member 12
NM_001710 B-factor, properdin
NM_006216 serine (or cysteine) proteinase inhibitor, clade E
NM_005110 glutamine-fructose-6-phosphate transaminase 2
AF506819 Homo sapiens URB mRNA, complete cds
NM_002074 guanine nucleotide binding protein, beta polypeptide 1
H26022 fractalkine, inducible cytokine subfamily D (Cys-X3-Cys)
AK092836 Homo sapiens cDNA FLJ35517 fis, clone SPLEN2000698
BQ890604 Homo sapiens URB mRNA, complete cds
AA057204 interleukin 2 receptor, beta
AI524093 myosin, heavy polypeptide 11, smooth muscle
AI655374 stromal cell-derived factor 1

--